United States Patent [19]

Gottier

[11] Patent Number: 4,654,062
[45] Date of Patent: Mar. 31, 1987

[54] HYDROCARBON RECOVERY FROM CARBON DIOXIDE-RICH GASES

[75] Inventor: Gerry N. Gottier, Allentown, Pa.

[73] Assignee: Air Products and Chemicals, Inc., Allentown, Pa.

[21] Appl. No.: 884,574

[22] Filed: Jul. 11, 1986

[51] Int. Cl.[4] .......................... F25J 3/02; C10B 17/16
[52] U.S. Cl. ............................................ 62/17; 62/20;
208/340; 208/341; 208/358; 423/220; 423/226; 55/68

[58] Field of Search .............. 208/313, 340, 341, 343, 208/350, 351, 353, 354, 357, 358; 423/220, 226; 62/17, 20, 24, 28, 11, 19, 12; 55/68, 73

[56] References Cited

U.S. PATENT DOCUMENTS

| | | | |
|---|---|---|---|
| 3,770,622 | 11/1973 | Freireich et al. | 208/340 |
| 4,254,094 | 3/1981 | Hegarty | 423/648 R |
| 4,293,322 | 10/1981 | Ryan et al. | 62/17 |
| 4,318,723 | 3/1982 | Holmes et al. | 62/20 |
| 4,350,511 | 9/1982 | Holmes et al. | 62/17 |
| 4,370,156 | 1/1983 | Goddin, Jr. et al. | 62/17 |
| 4,372,925 | 2/1983 | Cornelisse | 423/226 |
| 4,383,842 | 5/1983 | O'Brien | 62/20 |
| 4,428,759 | 1/1984 | Ryan et al. | 62/17 |
| 4,462,814 | 1/1984 | Holmes et al. | 62/17 |
| 4,557,911 | 12/1985 | Goddin, Jr. et al. | 423/220 X |

Primary Examiner—Glenn Caldarola
Attorney, Agent, or Firm—Geoffrey L. Chase; E. Eugene Innis; James C. Simmons

[57] ABSTRACT

A process is set forth for the separation of carbon dioxide from propane and higher alkanes using a carbon dioxide-loaded lean oil solvent and higher solvent flows and heat utilizations rather than mechanical energy utilization. A high pressure carbon dioxide product is produced, making the invention valuable in carbon dioxide miscible flood enhanced petroleum recovery operations.

16 Claims, 1 Drawing Figure

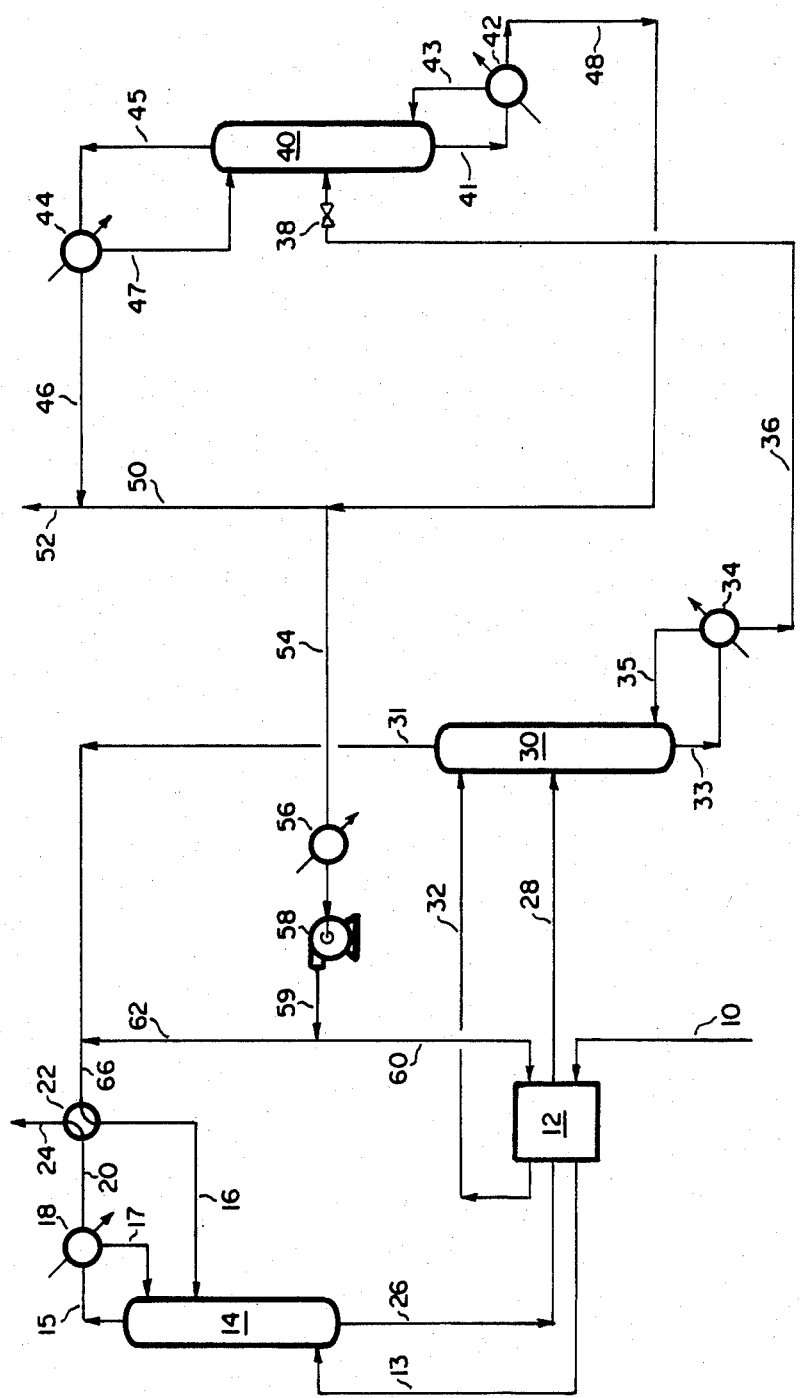

HYDROCARBON RECOVERY FROM CARBON DIOXIDE-RICH GASES

TECHNICAL FIELD

The present invention is directed to the recovery of lower alkane hydrocarbons from a carbon dioxide-containing gas stream using a carbon dioxide-loaded lean oil solvent to absorb the alkanes, while not absorbing the carbon dioxide. More specifically, the present invention is directed to a multicolumn separation of propane and higher molecular weight hydrocarbons from carbon dioxide in a carbon dioxide predominating gas stream using a carbon dioxide-loaded $C_{6+}$ lean oil solvent to initially effect such separation. The invention is further directed to achieving such separation utilizing higher solvent flow rates and higher heat input, but lower mechanical energy utilization than competing processes. The invention produces the carbon dioxide near feed pressure and is therefore particularly applicable for carbon dioxide miscible flooding of oil reservoirs in which carbon dioxide is required at elevated pressures.

BACKGROUND OF THE PRIOR ART

Various prior art teachings are directed to the separation of acid gases, and more specifically, separations of carbon dioxide from hydrocarbons including methane and lower alkanes. These methods typically utilize high levels of refrigeration to perform condensing duty in absorption and distillation columns effecting the appropriate separations and/or utilize lower molecular weight extractants, such as $C_4$ to $C_6$ alkanes to overcome various problems of relative volatility, azeotrope formation and triple point approach. Additionally, certain processes exist which require little or no refrigeration, but produce the carbon dioxide product at low pressure and require high levels of recompression energy to return the carbon dioxide to feed pressure.

One typical mode of effecting a carbon dioxide and lower alkane separation is refrigerated distillation which uses a carbon dioxide-rich liquid reflux from an overhead condenser to wash hydrocarbons from a carbon dioxide-containing stream. The refrigeration power for the overhead condenser becomes excessive at high propane recovery such that, for a high carbon dioxide feed containing about 1-2% propane, it is uneconomical to recover more than about 30% of the propane.

It is further known to use an activated MDEA (methyldiethanolamine) solvent in an absorption/stripping process to perform the specified separation. Carbon dioxide is absorbed from the gas stream at feed pressure, then the carbon dioxide-rich solution is dropped in pressure and in some cases, heated to liberate the carbon dioxide. The process is capable of very high hydrocarbon recoveries, but high capital and operating costs are incurred in recompressing the product carbon dioxide.

Additionally, it is known to utilize various membrane processes, wherein the process exploits the ability of certain materials to preferentially permeate carbon dioxide from carbon dioxide-hydrocarbon mixtures. The technique is capable of achieving high hydrocarbon recoveries. However, the carbon dioxide permeates the membrane at low pressure and must be recompressed. Again, this recompression is both capital and energy intensive.

Finally, it is known to use extractive distillation, such as is typically referred to as Ryan/Holmes processes. The extractive distillation involves addition of the recycled $C_4$-$C_6$ liquid alkane to the distillation column at a location above the feed. The extractive agent improves the relative volatility of carbon dioxide to propane and allows high recoveries to propane and higher alkanes. Approximately equivalent amounts of power and heat are required by the process when the recommended ratio of 10 moles of liquid agent per 100 moles of feed is employed. Small increases in the amount of solvent may decrease the power input somewhat, but the process becomes increasingly less efficient, and total energy needs increase substantially if solvent circulation is increased to a greater degree.

Relevant prior art includes U.S. Pat. No. 4,428,759 wherein in FIG. 2 a three column configuration of extractive distillation is performed of a feed stream comprising methane, ethane, nitrogen and carbon dioxide. The carbon dioxide, however, is removed as the bottom stream from the initial column, while nitrogen and methane are removed as an overhead through a condenser where the extractive agent is added. In the second column, additional extractive agent is added to such secondary distillation wherein a methane product is recovered as an overhead, and the carbon dioxide is removed to yet another or third column for separation from the $C_{4+}$ material in a distillation column, which is run by an overhead condenser and a bottom reboiler. FIG. 3 shows a two column extractive distillation of $CO_2$ and $C_3$.

In U.S. Pat. No. 4,293,322 a carbon dioxide-hydrogen sulfide separation is disclosed using an extractant of $C_3$-$C_6$ alkanes wherein in the initial column, carbon dioxide is removed as an overhead fraction and the extractant and the hydrogen sulfide removed as a bottom fraction for subsequent further separation in a black box configuration whereby the hydrogen sulfide is segregated from the extractant, which in turn is recycled to the initial distillation column.

U.S. Pat. No. 4,254,094 discloses the separation of synthesis gas-type feed strams into a hydrogen product, a carbon dioxide vent stream and a hydrogen sulfide by-product whereby in column 24 a carbon dioxide-loaded physical solvent is utilized to strip hydrogen sulfide without co-absorption of carbon dioxide contained in the feed to that column. Carbon dioxide is absorbed in the stage of the column directly above the hydrogen sulfide column, specifically the upper stage 25 of the overall column 23.

Additional art of less relevance, but disclosing light gas separations and multicolumn extractive distillation includes; U.S. Pat. Nos. 4,318,723, 4,370,156, 4,383,842 and 4,462,814.

None of the above-recited prior art disclosures provide an efficient, heat-based process to separate carbon dioxide from propane and lower molecular weight natural gas liquids. Furthermore, it is readily apparent from the literature that the need for such a process to economically integrate with the existing energy sources where the separation is to occur, has not been addressed. Thus, the potential for economic savings by using the low cost energy source contemplated from the present invention, has not yet been realized.

BRIEF SUMMARY OF THE INVENTION

The present invention is directed to a process for the lean oil absorptive separation of a carbon dioxide-rich feed stream into a carbon dioxide-enriched product and a $C_{3+}$ hydrocarbon-enriched product comprising the steps of contacting a carbon dioxide-rich feed stream containing lower molecular weight hydrocarbons with a carbon dioxide-loaded lean oil solvent in an absorption column, recovering a carbon dioxide-enriched stream at the overhead of said absorption zone and condensing a part of said stream as condensate to reflux said absorption zone while recovering a carbon dioxide-enriched product from the condensation step, cooling said carbon dioxide-loaded lean oil solvent by heat exchange with a lower temperature fluid, removing a $C_{3+}$ hydrocarbon-rich bottom stream from said absorption zone and contacting it in a stripping zone with additional lean oil solvent, removing a substantially carbon dioxide-containing stream from the overhead of said stripping zone, while recovering a substantially $C_{3+}$ hydrocarbon-containing stream at the bottom of said stripping zone, reboiling said stripping zone with a portion of said $C_{3+}$ hydrocarbon-containing stream, introducing the remaining $C_{3+}$ hydrocarbon-containing stream into a solvent recovery zone and recovering a $C_{3+}$ hydrocarbon-enriched product at the overhead of said zone while recovering a lean oil solvent at the bottom of said zone for recycle to said absorption zone and said stripping zone, combining a portion of said recycle lean oil solvent with said carbon dioxide-containing stream from said stripping zone to provide a carbon dioxide-loaded lean oil solvent which is introduced into said absorption zone, and introducing another portion of said lean oil solvent into said stripping zone.

Preferably, the carbon dioxide-rich feed stream is at a pressure of 200–600 psia.

Additionally, it is preferred that the carbon dioxide-rich feed stream is cooled to a temperature in the range of 0° to 50° F. by indirect heat exchange against process streams before entering the absorption zone.

Preferably, the lean oil solvent is a mixture of $C_4$–$C_8$ alkane hydrocarbons, optimally $C_6$–$C_8$ alkane hydrocarbons. Alternatively, the lean oil solvent may be an organosiloxane.

In a preferred embodiment, the carbon dioxide loading of the lean oil solvent involves a carbon dioxide content of 33 to 67% by weight of carbon dioxide in the solvent.

Preferably, the carbon dioxide-loaded lean oil solvent is cooled to a temperature in the range of $-10°$ to $40°$ F. by indirect heat exchange of said carbon dioxide-enriched product in order to recover essentially all the refrigeration value of the carbon dioxide-enriched product for utilization in the absorption separation.

The process of the present invention recovers better than 95% of the propane in the feed stream as a $C_{3+}$ hydrocarbon-enriched product.

Preferably, sufficient of the lean oil recovered as a bottom stream in the solvent recovery zone is blended with the $C_{3+}$ hydrocarbon-enriched product to produce a combined product such that lean oil components introduced in the feed stream do not accumulate in the system. Specifically, $C_6$ to $C_8$ hydrocarbons that are introduced in the feed stream to the separatory process are purged from the system by combining with the $C_{3+}$ hydrocarbon-enriched product.

Optimally, the absorptive separation in the initial column of the process of the present invention allows for the recovery of substantially all of the carbon dioxide in the feed stream at relatively high pressure and preferably at a pressure approximating the feed stream pressure.

BRIEF DESCRIPTION OF THE DRAWING

The drawing is a schematic flow scheme of a preferred embodiment of the present invention.

DETAILED DESCRIPTION OF THE INVENTION

The present invention utilizing a higher molecular weight lean oil solvent then the extractive distillations of Ryan-Holmes-type separations and utilizing a carbon dioxide-loaded lean oil solvent in the absorption zone provides efficient separations at reduced mechanical energy requirements by reducing the amount of reflux needed in the absorption zone through the efficient use of higher solvent circulation rates. Using less reflux and more solvent shifts the energy requirements of the process away from mechanical power and towards direct heat input. Since the process allows this trade-off to be accomplished in an efficient manner, overall energy consumption remains approximately the same as for an extractive distillation process. Substitution of the less expensive energy source for a more expensive one leads to a substantial decrease in operating cost.

In addition to reducing operating costs, the process also reduces capital outlay. The savings in power input translates into a reduction in size of the refrigeration unit needed to reflux the absorption zone. Thus, expensive compression machinery is minimized and is replaced with distillation and heat exchange equipment. Furthermore, in order for competing processes to use fuel as a power source, gas engines or turbines would be required to convert the fuel into power. Thus, the ability of the process of the present invention to use the fuel directly in a heat exchange mode, rather than in conversion to mechanical energy and then to refrigeration, results in additional savings in machinery.

Finally, the process allows the flexibility to adjust the ratio of power to heat input. Such flexibility is crucial to the integration of the process with associated systems, such as cogeneration or fuel powered injection compressors.

The process of the present invention differs from previous attempts to perform carbon dioxide and lower alkane separations by the use of preloaded solvent. This step reduces the amount of reflux required from the overhead condenser in two ways for an absorption column performing such separations. The flow rate of the preloaded solvent is higher than the flow rate of the lean solvent alone. Since the liquid rate in the column is an important parameter in determining the amount of propane and higher alkanes absorbed, increasing the amount of a liquid added to the column by preloading the solvent allows a corresponding decrease in the liquid which must be generated by the overhead condenser. Also, using a preloaded solvent prevents absorption of carbon dioxide from the feed, so a reboiler is not needed on the first column. The absence of a reboiler reduces the vapor flow in the column. Less liquid is required to absorb the hydrocarbons from the reduced vapor flow, so a further decrease in liquid rate is realized.

An additional difference is the utilization of a two-column scheme for separating carbon dioxide from propane and heavier hydrocarbons. The addition of a second column is necessary to carry out the solvent preloading scheme and allows the removal of the reboiler from the first column. As noted above, removal of the reboiler reduces the condenser duty on the first column. The separation of the carbon dioxide from the rich solvent is accomplished by the second column reboiler and solvent added to the second column. Thus, the use of the second column reduces the power needed in the first column condenser at the expense of additional heat input to the second column.

In addition, the use of a heavier solvent on the order of $C_6$ to $C_8$ provides benefit over the extractive distillation approaches that suggest using a $C_{4+}$ solvent. The use of such a solvent in this process of the present invention would be impractical due to the unacceptable solvent loss resulting from the lower liquid rate in the knock-down zone of the first column. Therefore, the heavier solvent is required to make the preloaded solvent scheme practical.

Finally, the present invention enjoys the recovery of product refrigeration because of the preloading step. In an extractive distillation scheme, only a portion of the available refrigeration in the carbon dioxide product stream can be recovered by precooling the lean solvent. The carbon dioxide absorption which occurs in the preloading step substantially increases the capacity of the solvent stream to absorb refrigeration, such that it can recover all the refrigeration available from the carbon dioxide product. Total recovery of the refrigeration from the carbon dioxide product stream leads to a reduction in the refrigeration which must be generated by the refrigeration unit and thus reduces power requirements.

The present invention will now be described in greater detail with reference to the drawing and a preferred embodiment which should not be deemed to be limiting of the invention, but merely illustrative of the invention. Feed stream 10, having a composition as identified in Table 1 below;

TABLE 1

| Component | Composition, Mole % |
|---|---|
| $N_2$ | 0.35 |
| $H_2S$ | 0.39 |
| $CO_2$ | 88.15 |
| $C_1$ | 3.98 |
| $C_2$ | 1.95 |
| $C_3$ | 2.69 |
| $C_4$ | 1.54 |
| $C_5$ | 0.61 |
| $C_6$ | 0.21 |
| $C_{7+}$ | 0.13 |
| | 100.00 |
| Flowrate: 3613 lb mol/hr | | is introduced at a pressure in the range of 200–600 psia and is cooled in heat exchanger 12 against process streams including lean oil solvent and a $C_{3+}$ hydrocarbon-rich stream to a temperature of about 0° F. to 50° F. and is then introduced in line 13 into the bottom section of an absorption zone comprising an absorption column 14. The carbon dioxide-rich feed stream contains lower molecular weight hydrocarbons per Table 1 and is contacted in the absorption column 14 with a carbon dioxide-loaded lean oil solvent. This solvent is introduced in line 16 into the upper stages of the column 14. The solvent absorbs $C_{3+}$ hydrocarbon components from the feed stream. The solvent may be a mixture of $C_4$ and heavier alkanes, but is preferably comprised of $C_6$ and heavier alkanes, such as a mixture of $C_6$ to $C_8$ alkanes. Alternatively, the solvent may be another suitable liquid agent such as an organosiloxane compound including Hexamethyldisiloxane $(CH_3)_3SiOSi(CH_3)_3$,
Octamethyltrisiloxane $(CH_3)_3SiO(CH_3)_2SiOSi(CH_3)_3$,
Polydimethylsiloxane $(CH_3)_3SiO[(CH_3)_2SiO]_xSi(CH_3)_3$,
Trifluoropropylmethylsiloxane $(CH_3)_3SiO(CH_3)(C_3H_4F_3)SiOSi(CH_3)_3$,
Hexaethyldisiloxane $(C_2H_5)_3SiOSi(C_2H_5)_3$ and
Polydiethylsiloxanes $(C_2H_5)_3SiO[(C_2H_5)_2SiO]_xSi(C_2H_5)_3$.

Stream 16 is typically about 33% to 67% carbon dioxide with a balance consisting of the lean oil solvent. It is typically cooled to about −10° F. to 40° F. in heat exchanger 22 before being introduced into column 14. Since the solvent stream 16 had been preloaded with carbon dioxide, the carbon dioxide in the feed stream 10 is not co-absorbed with the hydrocarbons by the solvent in column 14. A carbon dioxide-enriched overhead stream from said absorption column is removed in line 15 and cooled in heat exchanger or reflux condenser 18 against an outside cooling fluid such as ammonia, hydrocarbon or halofluorocarbon refrigerant. It is possible that the condensing duty could be in or integrated with the column. A part of stream 15 is condensed as the stream in line 17 and is returned as condensate to reflux the absorption column 14, while a carbon dioxide-enriched product in line 20 is removed from the condensation step occurring in reflux condenser 18 and is rewarmed in heat exchanger 22 to recover essentially all of the refrigeration value in the carbon dioxide-enriched product, which is then removed as a product of the process in line 24. The reflux condenser 18 is used in order to avoid solvent losses off the top of the column 14 by providing reflux to the solvent knock-back zone at the top of the column. The temperature in the condenser will be about −30° F. to 20° F. depending upon the amount of light gas in the feed and upon the pressure at which the column is operated. The carbon dioxide-enriched product 24 from which up to 95% of the propane and 95–100% of the $C_{4+}$ components in the feed gas have been removed is warmed to about 90° F. in the heat exchanger 22 while providing cooling for the solvent stream 66.

The $C_{3+}$ hydrocarbon-rich bottom stream in line 26, which is removed from said absorption column 14, is then rewarmed in the heat exchanger 12 against feed and lean oil solvent and contains the preloaded solvent and the $C_{3+}$ absorbed components from the feed. If column 14 is operated in the high pressure range of approximately 450–600 psia, the bottom stream in line 26 may be flashed to a lower pressure of approximately 200–400 psia. The temperaure of this stream is typically in the range of 10° F. to 40° F. and it is warmed to about 70° F. to 90° F. in the heat exchanger 12 before being introduced into a stripping zone or a stripping column 30 as stream 28. Much of the carbon dioxide contained in stream 28 has been vaporized by the warming step, and the remaining carbon dioxide is stripped from the liquid in stripping column 30. The stripping vapor for column 30 is provided by a reboil heat exchanger 34 operated at a temperature of approximately 300° F. to 500° F. The $C_{3+}$ hydrocarbon rich bottom stream and loaded solvent is contacted in the stripping column with additional lean oil solvent, which is not preloaded with carbon dioxide. A substantially carbon dioxide-containing stream in line 31 is removed from the overhead of said stripping column 30, and a substantially $C_{3+}$ hydrocarbon-containing stream is removed in line 33 from the bottom of said stripping column. Stream 33 is partially vaporized in reboil heat exchanger 34, and the vapor is returned to the column 30 in line 35. This provides reboil for column 30. Alternatively, the reboil function could be in or integrated directly with the column 30.

To avoid the loss of propane which is partially stripped along with the carbon dioxide in the column 30, the lean oil solvent stream in line 32, which has been cooled to about 20° F. to 70° F. in heat exchanger 12, is introduced into the top of column 30. Propane, which is stripped in the bottom of column 30, is thus reabsorbed by the lean oil solvent 32 in the upper section of the column 30. Consequently, the vapor product in line 31 from the column 30 contains essentially only the carbon dioxide which is used to preload the lean oil solvent.

The remaining $C_{3+}$ hydrocarbon-containing stream in line 36 is flashed through a throttling valve 38 to a pressure of about 40–200 psia. This stream is then introduced into the solvent recovery zone or solvent recovery column 40 for separation. The solvent recovery column 40 is operated with a reboiler 42 supplied with heat from an external source at about 200° F. to 450° F. Reflux is supplied from the overhead condenser 44 which typically operates at 100° F. to 200° F. and will generally use air or cooling water as the cooling source. Both the reboil and condensing duty can be in or integrated directly with the column 40.

Column 40 separates its feed into an overhead stream 45 comprising a $C_{3+}$ hydrocarbon-enriched product, which contains most of the natural gas liquid alkane hydrocarbon components recovered from the feed gas, and a lean oil solvent removed as a bottom stream in line 41, which contains most of the solvent, usually $C_6$–$C_8$ alkanes, along with a small amount of the heavier natural gas liquid product as well. The $C_{3+}$ hydrocarbon-enriched product in line 45 is partially condensed in the overhead condenser 44 and the liquid is returned in line 47 to reflux column 40. The remaining portion of the $C_{3+}$ hydrocarbon-enriched product is removed in line 46 for combination with a portion of the bottom stream from line 50 and removal of the combined streams in line 52 as the $C_{3+}$ hydrocarbon-enriched product containing propane and the natural gas liquids (higher $C_{4+}$ alkanes) desired as the hydrocarbon product of the overall process.

The bottom stream in line 41, which contains the lean oil solvent and preferably the $C_6$–$C_8$ hydrocarbons, is partially vaporized in reboil heat exchanger 42 and the vapor is returned in line 43 to reboil column 40. The remaining lean oil solvent in line 48 is recycled to the absorption zone or absorption column 14 and the stripping zone or column 30, but a portion of the recycle lean oil solvent in line 48 comprising a slipstream in line 50, is removed as a product with the $C_{3+}$ hydrocarbon-enriched product 46, in order to purge the overall system of any higher alkanes ($C_{6+}$) which come into the process in the feed stream. The remaining lean oil solvent in line 54 is cooled in solvent cooler 56 in which the solvent is cooled to about 100° F., typically against cooling water or air. The solvent pump 58 then boosts the pressure of the solvent up to the pressure of the stripping column 30. A portion of the solvent stream in line 59 is taken through line 60 to heat exchanger 12 in which it is cooled prior to introduction into the stripping column 30 in line 32. The remaining solvent in line 62 is combined with the stripping column overhead in line 31 to give the preloaded solvent stream 66. The carbon dioxide-loaded lean oil solvent is a two-phase stream in line 66 at approximately 100° F. It is cooled and condensed against the absorption column overhead product in line 20 in heat exchanger 22. The resulting cooled stream 16 is typically liquid at or below its bubble point temperature and serves as a preloaded solvent stream for the absorption column 14. If the operating pressure of the absorption column is greater than that of the stripping column, an additional pump will be required to boost the pressure of stream 16 accordingly. The product streams of the overall process are given in Table 2.

TABLE 2

Product Streams from $CO_2$—Loaded Lean Oil Process

| Composition, Mole % | $CO_2$—Enriched Product | $C_{3+}$ Hydrocarbon-Enriched Product |
|---|---|---|
| $N_2$ | 0.37 | — |
| $H_2S$ | 0.39 | 0.40 |
| $CO_2$ | 92.74 | 0.20 |
| $C_1$ | 4.19 | — |
| $C_2$ | 2.03 | 0.40 |
| $C_3$ | 0.28 | 48.83 |
| $C_4$ | 12 ppm | 31.04 |
| $C_5$ | 15 ppm | 12.28 |
| $C_6$ | 3 ppm | 4.23 |
| $C_{7+}$ | — | 2.62 |
| | 100.00 | 100.00 |
| Flowrate, lb mol/hr | 3433.9 | 179.1 |

The process of the present invention has been set forth with regard to a specific preferred embodiment. This invention enjoys various advantages over the prior art, particularly when utilized in the environment of enhanced oil recovery operations, where the separation may be occurring in an undeveloped region near a wellhead of a petroleum producing well. In these environments, energy in the form of electrical power or mechanical energy, is usually scarce and expensive, whereas because petroleum and natural gas products are being produced, heat energy from the combustion of such fuel sources is relatively less expensive and readily available. The process of the present invention reduces power requirements by 55% compared to similar extractive distillation processes recited in the prior art, while increasing heat input to the present invention by 36% over those same extractive distillations. The total energy requirement for the process of the present invention is about 11% lower than the energy requirement by those same extractive distillation processes. However, since fuel is less expensive than power for a typical enhanced oil recovery application, the process of the present invention can show substantially greater economic advantages. When waste heat is available from gas driven equipment typically utilized at a petroleum production site, the energy charge for this process will be quite low and advantageous over the known extractive distillation techniques.

The energy cost savings of the present invention over known extractive distillation techniques are realized by preloading the lean oil solvent with carbon dioxide and by splitting the carbon dioxide-propane separation into two steps; a first step in which propane is absorbed into the preloaded solvent and a second step in which the rich solvent is stripped of carbon dioxide. In the solvent preloading step, cooling is done by heat exchange with the carbon dioxide product, thus achieving efficient recovery of the refrigeration from the carbon dioxide product. The two-step separation allows the use of greater solvent flow rates than are feasible for extractive distillation. As a result, the process of the present invention uses less electrical power and more heat input than extractive distillation. Since fuel is generally less expensive than power, particularly in the environment of enhanced oil recovery applications, the process of the present invention will usually be more economical than extractive distillation.

The process of the present invention should not be deemed to be limited to the preferred embodiment set forth above, but rather the scope of the invention should be ascertained from the claims which follow.

I claim:

1. A process for the lean oil absorptive separation of a carbon dioxide-rich feed stream into a carbon dioxide-enriched product and a $C_{3+}$ hydrocarbon-enriched product comprising the steps of:
   (a) contacting a carbon dioxide-rich feed stream containing lower molecular weight hydrocarbons with a carbon dioxide-loaded lean oil solvent in an absorption zone;
   (b) recovering a carbon dioxide-enriched stream at the overhead of said absorption zone and condensing a part of said stream as condensate as reflux to said absorption zone while recovering a carbon dioxide-enriched product from the condensation step;
   (c) cooling said carbon dioxide-loaded lean oil solvent by heat exchange with a lower temperature fluid;
   (d) removing a $C_{3+}$ hydrocarbon-rich bottom stream from said absorption zone and contacting it in a stripping zone with additional lean oil solvent;
   (e) removing a substantially carbon dioxide-containing stream from the overhead of said stripping zone, while recovering a substantially $C_{3+}$ hydrocarbon-containing stream at the bottom of said stripping zone;
   (f) reboiling said stripping zone with a portion of said $C_{3+}$ hydrocarbon-containing stream;
   (g) introducing the remaining $C_{3+}$ hydrocarbon-containing stream into a solvent recovery zone and recovering a $C_{3+}$ hydrocarbon-enriched product at the overhead of said zone while recovering a lean oil solvent at the bottom of said zone for recycle to said absorption zone and said stripping zone;
   (h) combining a portion of said recycled lean oil solvent with said carbon dioxide-containing stream from said stripping zone to provide a carbon dioxide-loaded lean oil solvent which is introduced into said absorption zone; and
   (i) introducing another portion of said lean oil solvent into said stripping zone.

2. The process of claim 1 wherein said carbon dioxide-rich feed stream is at a pressure of 200–600 psia.

3. The process of claim 1 wherein said carbon dioxide-rich feed stream is cooled to a temperature in the range of 0° to 50° F. by indirect heat exchange against process streams before entering the absorption zone.

4. The process of claim 1 wherein said lean oil solvent is a mixture of $C_4$ to $C_8$ alkane hydrocarbons.

5. The process of claim 1 wherein said lean oil is substantially a mixture of $C_6$ to $C_8$ alkane hydrocarbons.

6. The process of claim 1 wherein said lean oil solvent is substantially an organosiloxane.

7. The process of claim 1 wherein said carbon dioxide-loaded lean oil solvent contains 33% to 67% by weight of carbon dioxide.

8. The process of claim 1 wherein said carbon dioxide-loaded lean oil solvent is cooled to a temperature in the range of $-10°$ to 40° F. by indirect heat exchange with said carbon dioxide-enriched product.

9. The process of claim 1 wherein said condensate of step (b) is cooled to a temperature in the range of $-30°$ to 20° F.

10. The process of claim 1 wherein up to 95% of the propane in said feed stream is recovered in said $C_{3+}$ hydrocarbon-enriched product.

11. The process of claim 1 wherein said remaining $C_{3+}$ hydrocarbon-containing stream is reduced in pressure prior to introduction into said solvent recovery zone.

12. The process of claim 1 wherein said solvent recovery zone is reboiled and refluxed by external heat and cooling sources respectively.

13. The process of claim 1 wherein a portion of said lean oil solvent from said solvent recovery zone is combined with said $C_{3+}$ hydrocarbon-enriched product.

14. The process of claim 1 wherein in step (c) said carbon dioxide-loaded lean oil solvent is cooled by indirect heat exchange with the rewarming carbon dioxide-enriched product.

15. The process of claim 1 wherein said $C_{3+}$ hydrocarbon-rich stream of step (d) is reduced in pressure prior to introduction into said stripping zone.

16. A process for the lean oil absorptive separation of a carbon dioxide-rich feed stream into a carbon dioxide-enriched product and a $C_{3+}$ hydrocarbon-enriched product comprising the steps of:
   (a) cooling a carbon dioxide-rich hydrocarbon feed stream to a temperature in the range of 0° to 50° F. by indirect heat exchange with process streams;
   (b) separating said feed stream in an absorption column using a carbon dioxide-loaded lean oil solvent comprising essentially $CO_2$ and $C_{6-8}$ alkanes and a reflux condenser to produce a carbon dioxide-enriched overhead stream and a $C_{3+}$ hydrocarbon-rich bottom stream;
   (c) cooling and partially condensing said carbon dioxide-enriched overhead stream in a reflux condenser wherein the gas phase stream is removed as a carbon dioxide-enriched product at approximately feed stream pressure and the liquid phase stream is returned to said absorption column as reflux;
   (d) recovering refrigeration from said carbon dioxide-enriched product by indirect heat exchange with said carbon dioxide-loaded lean oil solvent prior to said solvents introduction into said absorption column so as to rewarm said product and cool said solvent;
   (e) removing a $C_{3+}$ hydrocarbon-rich stream and the carbon dioxide-loaded lean oil solvent in a mixture as a bottom stream from said absorption column and rewarming it to a temperature of 70° to 90° F. by indirect heat exchange with process streams;
   (f) separating said bottom stream in a carbon dioxide stripper column using a lean oil solvent and a reboiler to produce a substantially carbon dioxide-containing stream from the overhead of said stripping column and a substantially $C_{3+}$ hydrocarbon and lean oil-containing stream from the bottom of said stripping column;

(g) reboiling said substantially $C_{3+}$ hydrocarbon and lean oil-containing stream in a reboil heat exchanger to return a portion of said stream as reboil vapor to said stripping column while the remainder of said stream is removed for further recovery;

(h) reducing said remaining stream of step (g) in pressure and separating it in a solvent recovery column operated with a reflux condenser and a reboil heat exchanger so as to produce a substantially $C_{3+}$ hydrocarbon stream diminished in $C_{6-8}$ alkane hydrocarbons as an overhead stream and a substantially $C_{6-8}$ alkane lean oil stream as a bottom stream;

(i) removing a minor slip stream from said substantially $C_{6-8}$ alkane lean oil stream and combining it with said substantially $C_{3+}$ hydrocarbon stream as a $C_{3+}$ hydrocarbon-enriched product; and (j) recycling the remaining $C_{6-8}$ alkane lean oil stream in part to said stripper column and in part for combination with said substantially carbon dioxide-containing stram from said stripping column for introduction into said absorber column as the carbon dioxide-loaded lean oil solvent.

* * * * *